United States Patent [19]

Magruder

[11] 4,366,159
[45] Dec. 28, 1982

[54] NALBUPHINE-NARCOTIC ANALGESIC COMPOSITION AND METHOD OF PRODUCING ANALGESIA

[75] Inventor: Michael R. Magruder, 2035-A Taylor Run, Camp Springs, Md. 20335

[73] Assignee: Michael Richard Magruder, Camp Springs, Md.

[21] Appl. No.: 300,394

[22] Filed: Sep. 8, 1981

[51] Int. Cl.$^3$ ............................................ A61K 31/485
[52] U.S. Cl. ..................................................... 424/260
[58] Field of Search ......................................... 424/260

[56] References Cited

U.S. PATENT DOCUMENTS

| | | |
|---|---|---|
| 3,393,197 | 7/1968 | Pachter et al. ................... 260/285 |
| 3,493,657 | 2/1970 | Lewenstein et al. ............. 424/260 |
| 3,773,955 | 11/1973 | Pachter et al. .................. 424/260 |
| 3,879,555 | 4/1975 | Pachter et al. .................. 424/260 |
| 3,966,940 | 6/1976 | Pachter et al. .................. 424/260 |
| 4,237,140 | 12/1980 | Dudzinski ...................... 424/260 |
| 4,282,215 | 8/1981 | Dudzinski ...................... 424/232 |

OTHER PUBLICATIONS

J. Med. (Basel), 1, 74–89 (1970), Elliott et al.
Pharmacologist 10, 189, Fall 1968, Blumberg et al.
Drugs of the Future, 2, 613–615, (1977) Roberts.

*Primary Examiner*—Stanley J. Friedman

[57] ABSTRACT

A narcotic analgesic composition particularly in oral dosage form is provided which provides excellent analgesia in a mammal while reducing or eliminating the respiratory depression and euphoria usually associated with narcotic analgesics. The composition comprises an analgesic effective amount of a narcotic analgesic or salt thereof and an analgesic effective amount of nalbuphine or a salt thereof.

A method of producing analgesia in a mammal is also provided, this method comprises administering to a mammal parenterally or orally an analgesic effective amount of a narcotic analgesic or salt thereof and an analgesic effective amount of nalbuphine or a salt thereof. Administration of the narcotic analgesic and nalbuphine can be either sequentially or simultaneously.

10 Claims, 1 Drawing Figure

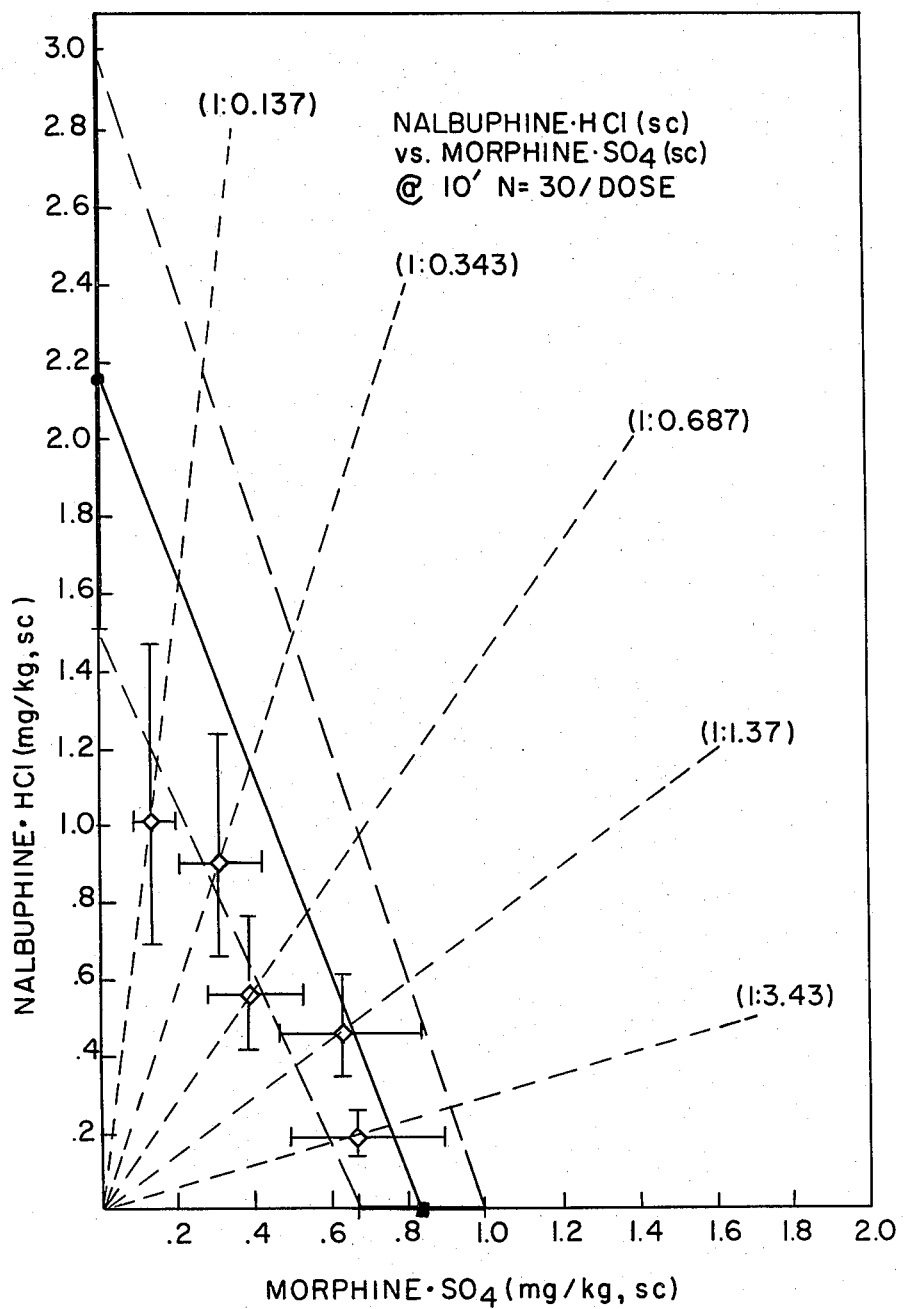

NALBUPHINE-NARCOTIC ANALGESIC COMPOSITION AND METHOD OF PRODUCING ANALGESIA

BACKGROUND OF THE INVENTION

1. Field of the Invention

This invention relates to analgesic compositions and methods of producing analgesia in mammals and more particularly to nalbuphine-narcotic analgesic oral compositions for producing analgesia in mammals.

2. Prior Art

U.S. Pat. No. 3,393,197 issued to Pachter and Matossian on July 16, 1968 discloses N-substituted-14-hydroxydihydronormorphines, including the N-cyclobutylmethyl derivatives, commonly called nalbuphine:

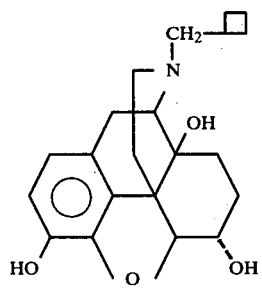

Pachter and Matossian and others, such as H. W. Elliott, et al., *J. Med.* (Basel), 1, 74–89 (1970); H. Blumberg, et al., *Pharmacologist*, 10, 189, Fall 1968; P. Roberts, *Drugs of the Future*, 2, 613–5 (1977), disclose the use of nalbuphine as an analgesic for the control of moderate to severe pain.

U.S. Pat. No. 4,237,140, issued to J. R. Dudzinski on Dec. 2, 1980, describes an analgesic mixture of nalbuphine and acetoaminophen. U.S. Pat. No. 4,282,215, issued to J. R. Dudzinski and W. K. Schmidt on Aug. 4, 1981, describes an analgesic mixture of nalbuphine and aspirin.

Morphine, oxymorphone, oxycodone and hydromorphone are well known strong narcotic analgesics which can, unfortunately, be addictive and/or euphoric and subjected to abuse by parenteral administration. Furthermore, these narcotics tend to produce respiratory depression in patients, especially when given as part of anesthesia. One attempt to minimize abuse of these and other strong analgesic agents is described in U.S. Pat. No. 3,773,955, issued to Pachter and Gordon on Nov. 20, 1973 (also U.K. Pat. No. 1,353,815) wherein a combination of a parenterally effective but orally ineffective dose of naloxone and an analgetic agent gives an orally effective, but parenterally inactive analgesic composition. While naloxone will overcome the narcotic analgesic upon parenteral administration to reduce respiratory depression, euphoria and other side effects, it also eliminates analgesia. Such a composition upon oral administration provides analgesia, but the naloxone is inactive orally such that there is no reduction in side effects.

B. J. Kripke et al., *J. of the International Anesthesia Research Society*, Vol. 55, No. 6, pages 800–805 November–December 1976, describe naloxone antagonism after narcotic-supplemented anesthesia.

SUMMARY OF THE INVENTION

According to the present invention, there is provided an analgesic composition which comprises an analgesic effective amount of a narcotic analgesic selected from the group consisting of morphine, oxymorphone, oxycodone, hydromorphone and a pharmaceutically suitable salt of one of the above, and an analgesic effective amount of nalbuphine or a pharmaceutically suitable salt thereof.

There is also provided a method of producing analgesia in a mammal comprising administering to a mammal an analgesic effective amount of a narcotic analgesic selected from the group consisting of morphine, oxymorphone, oxycodone, hydromorphone and a pharmaceutically suitable salt of one of the above, and an analgesic effective amount of nalbuphine or a pharmaceutically suitable salt thereof.

BRIEF DESCRIPTION OF THE DRAWING

The drawing is a graph showing the interaction of nalbuphine hydrochloride and morphine sulfate on the phenyl-p-benzoquinone induced writhing in mice.

DETAILED DESCRIPTION OF THE INVENTION

Nalbuphine, which has the chemical name (−)-17-(cyclobutylmethyl)-4,5α-epoxymorphinan-3,6α,14-triol, and its preparation are described in U.S. Pat. No. 3,393,197. It and the narcotic analgesics useful in the analgesic compositions of the present invention, i.e., morphine, oxymorphone, oxycodone and hydromorphone, all are well-known to have analgetic properties in man and other mammals.

When the term nalbuphine or the name of one of the above narcotic analgesics is used herein, it is to be understood that any of the pharmaceutically suitable salts thereof are included by the term. Such salts include the hydrochlorides, hydrobromides, hydroiodides, sulfates, bisulfates, nitrates, citrates, tartrates, bitartrates, phosphates, malates, maleates, fumarates, succinates, acetates and pamoates.

The compositions of the present invention are made into a dosage form to be taken orally or parenterally (preferably orally) by mixing an effective analgesic amount of nalbuphine with an effective analgesic amount of morphine, oxymorphone, oxycodone or hydromorphone. The amount of nalbuphine in each dosage form whether to be administered orally or parenterally will be about 1–100 mg, preferably about 5–60 mg while the amount of narcotic analgesic will be as follows:

(a) about 1–100 mg, preferably about 5–60 mg, of morphine;

(b) about 0.1–20 mg, preferably about 0.5–10 mg, of oxymorphone;

(c) about 0.5–50 mg, preferably about 2.5–30 mg, of oxycodone; or (d) about 0.1 ∝ 20 mg, preferably about 0.5–10 mg, of hydromorphone.

The compositions of the present invention can be formulated into any of the known pharmaceutical forms suitable for oral administration. The term "oral dosage form" includes solid compositions for oral administration in unit dosage form such as tablets, capsules, granules, powders and cachets or in liquid dosage form such as elixirs, syrups and suspensions. Bulk powders of fixed composition for subdivision into solutions, emulsions or suspensions of the composition are also included in the definition.

The oral compositions of the present invention can also optionally contain other ingredients such as aspirin, acetaminophen, phenacetin, caffeine, antihistamines, homatropine, methylbromide, phenyltoloxamine citrate, barbiturates, or mixtures thereof. The compositions can also contain other CII narcotics such as fentanyl, codeine, meperidine, methadone, etc.

Combining nalbuphine with morphine, oxymorphone, oxycodone, or hydromorphone in a composition maintains the excellent analgesia of the narcotic while reducing or eliminating the respiratory depression and euphoria usually associated with narcotics. This is surprising since nalbuphine is known to have narcotic antagonistic properties as well as analgesic properties. Thus, an advantage of the composition is excellent analgesia with reduced side effects. A further advantage is its greatly reduced susceptibility to abuse by a narcotic addict who tries to feed his habit by the parenteral route (mainlining). Nalbuphine is at least as long acting as, for example, morphine. Thus, as long as the nalbuphine is in a mammal's system, it will override the respiratory depression and euphoric properties of the narcotic without diminishing analgesia. In other words, an addict's attempt at mainlining will produce withdrawal for a long time. These aforesaid advantages also provide a safety factor in that large doses of the powerful narcotic analgesics can be given safely for analgesia in combination with nalbuphine and not cause significant respiratory depression later since the nalbuphine will always be present to protect the respiratory centers. This is particularly advantageous in the administration of anesthesia.

The present invention also provides a method of producing analgesia in a mammal by administering morphine, oxymorphone, oxycodone or hydromorphone in combination with nalbuphine in analgesic effective amounts. This administration can be simultaneous as will be the case when the preferred oral analgesic composition of the present invention is administered to the mammal. However, administration can also be sequential, i.e., administration of the narcotic analgesic followed later by nalbuphine, or vice versa, as well as parenteral. Parenteral, sequential administration will be a particularly useful method in anesthesia where the narcotic analgesic can be given i.v. in the usual manner followed by nalbuphine given i.v. to reverse respiratory depression if the need arises. Of course, the optimum dose for parenteral administration will change somewhat from the oral dose; however, these will be well known to those skilled in the pharmaceutical art.

Dosage Forms

The active ingredients can be administered orally in solid dosage forms, such as capsules, tablets, and powders, or in liquid dosage forms, such as elixirs, syrups and suspensions; they can also be administered parenterally, in sterile liquid dosage forms.

Gelatin capsules can contain the active ingredients and powdered carriers, such as lactose, sucrose, mannitol, starch, cellulose, derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solution for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and sodium EDTA. In addition, parenteral solutions can contain preservatives, such as benzalkonium chloride, methyl or propyl-paraben, and chlorobutanol.

Suitable pharmaceutical carriers are described in Remington's Pharmaceutical Sciences, E. W. Martin, a standard reference text in this field.

Useful pharmaceutical dosage-forms for administration of the compounds of this invention can be illustrated as follows:

CAPSULES

A large number of unit capsules can be prepared by filling standard two-piece hard gelatin capsules each with 15 mg nalbuphine or a pharmaceutically suitable salt and 10 mg morphine or a pharmaceutically suitable salt. Other inactive components of the formulation consist of 150.5 mg lactose, 90 mg microcrystalline cellulose (as diluents), 1.5 mg colloidal silicon dioxide (glidant), 30 mg corn starch (disintegrant) and 3 mg magnesium stearate (lubricant).

CAPSULES

A mixture of active ingredients in soybean oil can be prepared and injected by means of a positive displacement pump into gelatin to form soft gelatin capsules containing 15 mg nalbuphine and 10 mg morphine as active ingredients. The capsules can be washed in petroleum ether and dried.

TABLETS

A large number of tablets can be prepared by conventional procedures so that dosage unit is 15 mg nalbuphine or a pharmaceutically suitable salt and 10 mg morphine or a pharmaceutically suitable salt. Other components being 150 mg lactose and 90.5 mg microcrystalline cellulose (diluents), 30 mg starch (disintegrant) and 3.5 mg stearic acid, 1.5 mg magnesium stearate (lubricant). Appropriate coatings may be applied to increase palatability or delay absorption.

Injectables

1. A parenteral composition suitable for administration by injection can be prepared by dissolving 1–100 mg of nalbuphine or a pharmaceutically suitable salt and 1–100 of morphine or a pharmaceutically suitable salt form in an aqueous solution. Cosolvents such as propylene glycol may be added along with a preservative e.g., parabens, buffer e.g. citrate, stabilizing agents e.g. sodium metabisulfite and EDTA. Sodium chloride or other agents may be used to adjust isotonicity. The resulting solution can be terminally sterilized or sterilized by filtration.

Suspension

1. An aqueous suspension is prepared for oral administration such that each 5 milliliters contains 1 to 100 mg of finely divided nalbuphine or a pharmaceutically suitable salt and 1–100 mg morphine or a pharmaceutically suitable salt suspended with a suitable agent such as sodium carboxymethyl cellulose. Protective colloide e.g. methylcellulose, surfactants e.g. Tween 80, preservatives e.g. sodium benzoate, viscosity enhancing agents e.g. sorbital, flavoring agents e.g. vanillin, stabilizers e.g. EDTA along with a buffer e.g. phosphate and sweetener may be required to prepare a suitable formulation.

CAPSULES

A large number of unit capsules can be prepared by filling standard two-piece hard gelatin capsules each with 15 mg nalbuphine or a pharmaceutically suitable salt and 10 mg of oxymorphone or a pharmaceutically suitable salt. Other inactive components of the formulation consist of 150.5 mg lactose, 90 mg microcrystalline cellulose (as diluents), 1.5 mg colloidal silicon dioxide (glidant), 30 mg corn starch (disintegrant) and 3 mg magnesium stearate (lubricant).

CAPSULES

A mixture of active ingredients in soybean oil can be prepared and injected by means of a positive displacement pump into gelatin to form soft gelatin capsules containing 15 mg nalbuphine and 10 mg oxymorphone as active ingredients. The capsules can be washed in petroleum ether and dried.

TABLETS

A large number of tablets can be prepared by conventional procedures so that dosage unit is 15 mg nalbuphine or a pharmaceutically suitable salt and 10 mg oxymorphone or a pharmaceutically suitable salt. Other components being 150 mg lactose and 90.5 microcrystalline cellulose (diluents), 30 mg starch (disintegrant) and 3.5 mg stearic acid, 1.5 mg magnesium stearate (lubricant). Appropriate coatings may be applied to increase palatability or delay absorption.

Injectables

2. A parenteral composition suitable for administration by injection can be prepared by dissolving 1–100 mg of nalbuphine or a pharmaceutically suitable salt and 0.1–20 mg of oxymorphone or a pharmaceutically suitable salt form in an aqueous solution. Cosolvents such as propylene glycol may be added along with a preservative e.g., parabens, buffer e.g. citrate, stabilizing agents e.g. sodium metabisulfite and EDTA. Sodium chloride or other agents may be used to adjust isotonicity. The resulting solution can be terminally sterilized or sterilized by filtration.

Suspension

2. An aqueous suspension is prepared for oral administration such that each 5 milliliters contains 1 to 100 mg of finely divided nalbuphine or a pharmaceutically suitable salt and 0.1–20 mg oxymorphone or a pharmaceutically suitable salt suspended with a suitable agent such as sodium carboxymethyl cellulose. Protective colloide e.g. methylcellulose, surfactants e.g. Tween 80, preservatives e.g. sodium benzoate, viscosity enhancing agents e.g. sorbital, flavoring agents e.g. vanillin, stabilizers e.g. EDTA along with a buffer e.g. phosphate and sweetener may be required to prepare a suitable formulation.

CAPSULES

A large number of unit capsules can be prepared by filling standard two-piece hard gelatin capsules each with 15 mg nalbuphine or a pharmaceutically suitable salt and 5 mg oxycodone or a pharmaceutically suitable salt. Other inactive components of the formulation consist of 155.5 mg lactose, 90 mg microcrystalline cellulose (as diluents), 1.5 mg colloidal silicon dioxide (glidant), 30 mg corn starch (disintegrant) and 3 mg magnesium stearate (lubricant).

CAPSULES

A mixture of active ingredients in soybean oil can be prepared and injected by means of a positive displacement pump into gelatin to form soft gelatin capsules containing 15 mg nalbuphine and 5 mg oxycodone as active ingredients. The capsules can be washed in petroleum ether and dried.

TABLETS

A large number of tablets can be prepared by conventional procedures so that dosage unit is 15 mg nalbuphine or a pharmaceutically suitable salt and 5 mg oxycodone or a pharmaceutically suitable salt. Other components being 155 mg lactose and 90.5 microcrystalline cellulose (diluents), 30 mg starch (disintegrant) and 3.5 mg stearic acid, 1.5 mg magnesium stearate (lubricant). Appropriate coatings may be applied to increase palatability or delay absorption.

Injectables

3. A parenteral composition suitable for administration by injection can be prepared by dissolving 1–100 mg of nalbuphine or a pharmaceutically suitable salt and 0.5–50 mg oxycodone or a pharmaceutically suitable salt form in an aqueous solution. Cosolvents such as propylene glycol may be added along with a preservative e.g., parabens, buffer e.g. citrate, stabilizing agents e.g. sodium metabisulfite and EDTA. Sodium chloride or other agents may be used to adjust isotonicity. The resulting solution can be terminally sterilized or sterilized by filtration.

Suspension

3. An aqueous suspension is prepared for oral administration such that each 5 milliliters contains 1 to 100 mg of finely divided nalbuphine or a pharmaceutically suitable salt and 0.5–50 mg oxycodone or a pharmaceutically suitable salt suspended with a suitable agent such as sodium carboxymethyl cellulose. Protective colloide e.g. methylcellulose, surfactants e.g. Tween 80, preservatives e.g. sodium benzoate, viscosity enhancing agents e.g. sorbital, flavoring agents e.g. vanillin, stabilizers e.g. EDTA along with a buffer e.g. phosphate and sweetener may be required to prepare a suitable formulation.

CAPSULES

A large number of unit capsules can be prepared by filling standard two-piece hard gelatin capsules each with 15 mg nalbuphine or a pharmaceutically suitable salt and 4 mg hydromorphone or a pharmaceutically suitable salt. Other inactive components of the formulation consist of 156.5 mg lactose, 90 mg microcrystalline cellulose (as diluents), 1.5 mg colloidal silicon dioxide (glidant), 30 mg corn starch (disintegrant) and 3 mg magnesium stearate (lubricant).

CAPSULES

A mixture of active ingredients in soybean oil can be prepared and injected by means of a positive displacement pump into gelatin to form soft gelatin capsules containing 15 mg nalbuphine and 4 mg hydromorphone as active ingredients. The capsules can be washed in petroleum ether and dried.

TABLETS

A large number of tablets can be prepared by conventional procedures so that dosage unit is 15 mg nalbuphine or a pharmaceutically suitable salt and 4 mg hydromorphone or a pharmaceutically suitable salt. Other components being 156 mg lactose and 90.5 mg microcrytalline cellulose (diluents), 30 mg starch (disintegrant) and 3.5 mg stearic acid, 1.5 mg magnesium stearate (lubricant). Appropriate coatings may be applied to increase palatability or delay absorption.

Injectables

4. A parenteral composition suitable for administration by injection can be prepared by dissolving 1–100 mg of nalbuphine or a pharmaceutically suitable salt and 0.1–20 mg of hydromorphone or a pharmaceutically suitable salt form in an aqueous solution. Cosolvents such as propylene glycol may be added along with a preservative e.g., parabens, buffer e.g. citrate, stabilizing agents e.g. metabisulfite and EDTA. Sodium chloride or other agents may be used to adjust isotonicity. The resulting solution can be terminally sterilized for sterilized by filtration.

Suspension

4. An aqueous suspension is prepared for oral administration such that each 5 milliliters contains 1 to 100 mg of finely divided nalbuphine or a pharmaceutically suitable salt and 0.1–20 mg hydromorphone or a pharmaceutically suitable salt suspended with a suitable agent such as sodium carboxymethyl cellulose. Protective colloide e.g. methylcellulose, surfactants e.g. Tween 80, preservatives e.g. sodium benzoate, viscosity enhancing agents e.g. sorbital, flavoring agents e.g. vanillin, stabilizers e.g. EDTA along with a buffer e.g. phosphate and sweetener may be required to prepare a suitable formulation.

UTILITY

EXAMPLE 1

Test Methods

The unexpectedly additive analgetic activity obtained in the method of the invention is evidenced by tests conducted on mice. Male CF1 mice obtained from Charles River Breeding Laboratories, fasted for 16–22 hours and weighing 18–22 g at the time of testing are used throughout. All mice are dosed subcutaneously (s.c.) with nalbuphine hydrochloride and/or morphine sulfate dissolved completely in saline and pre-mixed at the dose ratios stated. A dosing volume of 10 ml/kg is used. All doses are coded and the test is performed under a code not known to the observer.

ANALGESIC ACTIVITY IN THE MOUSE ANTIPHENYLQUINONE WRITHING TEST

A standard procedure for detecting and comparing the analgesic activity of different classes of analgesic drugs for which there is a good correlation with human efficacy is the prevention of phenyl-p-benzoquinone induced writhing in mice (H. Blumberg et al.,; *Proc. Soc. Exp. Biol. Med.* 118, 763–766, 1965).

Mice, injected s.c. with various doses of nalbuphine hydrochloride, morphine sulfate, combined doses of nalbuphine hydrochloride and morphine sulfate, or vehicle, are injected intraperitoneally with a challenge dose of phenyl-p-benzoquinone. The phenyl-p-benzoquinone is prepared as a 0.1 mg/ml solution in 5% by volume of ethanol in water; the writhing dose is 1.25 mg/kg injected at the rate of 0.25 ml20 g. For scoring purposes a "writhe" is indicated by whole body stretching of contractions of the abdomen; mice are observed 10 minutes for the presence or absence of writhing beginning 5 minutes after receiving the phenyl-p-benzoquinone dose. Each mouse is used only once, then discarded.

All ED50 values are determined numerically by the moving average method of Thompson (W. F. Thompson: *Bacteriological Rev.* 11, 115–145, 1947) and 95% confidence limits are calculated according to the method of Litchfield and Wilcoxon (J. T. Litchfield, Jr. and F. Wilcoxon: *J. Pharm. Exp. Ther.* 96, 99–113, 1949). As used herein ED50 means the dosage at which 50% of the mice in a test group exhibit an analgesic response.

In order to study the interaction between nalbuphine and morphine, precise dosage ratios of nalbuphine hydrochloride and morphine sulfate are selected. Five coded doses of each selected combination are studied for analgesic effectiveness at 10 minutes (the predicted peak effect time) using an experimental design which permits complete randomization of the separate dosage forms tested. Altogether 35 separate dosage forms are used and each form is represented in each experimental session. The experiments are continued by running experimental sessions with an equal number of mice being tested for each dosage group until the total number, N, of mice tested per group is 30.

The interaction of nalbuphine hydrochloride and morphine sulfate on phenyl-p-benzoquinone induced writhing in mice is demonstrated by the data in Table I and in the Loewe isobologram (S. Loewe: *Pharm. Rev.* 9: 237–242, 1957) in the drawing. In the drawing, the diagonal line joining the ED50 values of the two drugs given separately represents the theoretical line for simple additivity of drug effects. The dashed lines on each side of the diagonal line give the 95% confidence limits for this line of additivity. ED50's falling under the curve (between the line and the origin) would indicate potentiation (enhancement) of effects while those outside of the curve would suggest antagonism between the two drugs. The 5 diagonal lines radiating from the origin represent the dose ratios of nalbuphine hydrochloride and morphine sulfate used in mice receiving the combined drug dosages. The horizontal and vertical bars through each ED50 point are the 95% confidence limits. The drawing shows that in the method of the invention, compositions having a weight ratio of nalbuphine hydrochloride to morphine sulfate from 1:0.137 to 1:3.43 give unexpectedly additive analgesic activity since the 95% confidence limits of the ED50 values for those ratios overlap the line of additivity.

values, 2 mg/kg of morphine sulfate was given subcutaneously and after 30 minutes, repeat measurements of

TABLE I
SUBCUTANEOUS NALBUPHINE/MORPHINE COMBINATIONS IN THE MOUSE ANTIPHENYLQUINONE WRITHING TEST
(N = 30 Mice/Dose)

| DRUG COMBINATIONS Nalbuphine HCl: Morphine SO4 | DRUG Dose (mg/kg) Nalbuphine HCl | Morphine SO4 | % MICE BLOCKED | ED50 AT 10 MIN. (95% Conf. Limits) Nalbuphine HCl | Morphine SO4 |
|---|---|---|---|---|---|
| Control (Saline) | 0 | 0 | 10% | — | — |
| 1:0 | 0.543 | 0 | 37% | 2.17 mg/kg | — |
| (Nalbuphine | 1.09 | 0 | 27% | (1.55– | |
| HCl only) | 2.17 | 0 | 50% | 3.03) | |
| | 4.34 | 0 | 67% | | |
| | 8.68 | 0 | 77% | | |
| 1:0.137 | 0.452 | 0.062 | 43% | 1.01 mg/kg | 0.139 mg/kg |
| | 0.904 | 0.124 | 37% | (0.694– | (0.096– |
| | 1.81 | 0.248 | 73% | 1.47) | 0.202) |
| | 3.62 | 0.497 | 77% | | |
| | 7.23 | 0.993 | 73% | | |
| 1:0.343 | 0.362 | 0.124 | 20% | 0.902 mg/kg | 0.310 mg/kg |
| | 0.723 | 0.248 | 40% | (0.657– | (0.226– |
| | 1.45 | 0.497 | 67% | 1.24) | 0.425) |
| | 2.89 | 0.993 | 93% | | |
| | 5.79 | 1.99 | 93% | | |
| 1:0.687 | 0.271 | 0.186 | 20% | 0.562 mg/kg | 0.386 mg/kg |
| | 0.543 | 0.373 | 47% | (0.410– | (0.281– |
| | 1.09 | 0.745 | 80% | 0771) | 0.530) |
| | 2.17 | 1.49 | 83% | | |
| | 4.34 | 2.98 | 97% | | |
| 1:137 | 0.181 | 0.248 | 27% | 0.460 mg/kg | 0.632 mg/kg |
| | 0.362 | 0.497 | 50% | (0.344– | (0.473– |
| | 0.723 | 0.993 | 50% | 0.614) | 0.844) |
| | 1.45 | 1.99 | 93% | | |
| | 2.89 | 3.97 | 100% | | |
| 1:3.43 | 0.0904 | 0.310 | 20% | 0.193 mg/kg | 0.662 mg/kg |
| | 0.181 | 0.620 | 37% | (0.142– | (0.485– |
| | 0.362 | 1.24 | 93% | 0.263) | 0.903) |
| | 0.723 | 2.48 | 100% | | |
| | 1.45 | 4.97 | 100% | | |
| 0:1 | 0.373 | 0 | 17% | — | 0.832 mg/kg |
| (Morphine | 0.745 | 0 | 37% | | (0.671– |
| SO4 | 1.49 | 0 | 83% | | 1.03) |
| only) | 2.98 | 0 | 100% | | |

EXAMPLE 2

The effect on anesthetic requirements and $PaCO_2$ of combined doses of nalbuphine hydrochloride and morphine sulfate was evaluated in 18 Sprague-Dawley rats (200–350 gms). Anesthetic requirements for cyclopropane anesthetic of each rat was determined using a tail-clamp technique (Munson et al., The Effect of Acute Hypothyroidism and Hyperthyoidism on Cyclopropane Requirements (MAC) in Rats, *Anesthesiology* 1968; 29:1094–1098). After induction of anesthesia with cyclopropane, the femoral artery and vein were exposed and catheterized with PE50 tubing. Anesthetic requirement as measured by minimal alveolar concentration (MAC) was determined and thereafter nalbuphine hydrochloride was administered intravenously. Upon completion of control measurements, a bolus dose of 0.04 mg/kg of nalbuphine hydrochloride was followed with a constant infusion of 0.1 mg/kg/min. After 45 minutes of continuous infusion, MAC was redetermined and arterial blood sampling repeated. The rat then received either 2, 4 or 8 mg/kg subcutaneously of morphine sulfate and after 30 minutes MAC and arterial blood gas (ABG) values ($PaO_2$, $PaCO_2$, pH, $HCO_3$) redetermined.

The effect of morphine sulfate alone on anesthetic requirement and respiration was evaluated in a separate group of five Sprague-Dawley rats. After baseline measurements of anesthetic requirement (MAC) and ABG anesthetic requirements and blood gases were carried out. For comparative purposes, the anesthetic requirements from a previous, similar study are included.

Statistical evaluation was carried out using analysis of variance comparing the groups of animals at different infusion rates of nalbuphine hydrochloride, and for the animals receiving the combined morphine sulfatenalbuphine hydrochloride doses. The results are shown in Table II.

TABLE II
Anesthetic and Respiratory Effect of Nalbuphine, Morphine and Nalbuphine plus Morphine

| | MAC Reduction % (Mean ± SEM) | $PaCO_2$ - mmHg (Mean ± SEM) |
|---|---|---|
| Nalbuphine HCl 0.1 mg/kg/min. | 21.62 ± 0.69 | 48.31 ± 1.07 |
| Morphine SO4 sc injection | | |
| 2 mg/kg | 22 ± 0.55 | 53 ± 1.05 |
| 2 mg/kg* | 21.80 ± 1.48 | — |
| 4 mg/kg* | 32.63 ± 0.98 | — |
| 8 mg/kg* | 54.87 ± 1.94 | — |
| Nalbuphine HCL 0.1 mg/kg/min. and Morphine SO4 sc injection | | |
| 2 mg/kg | 22.60 ± 1.29 | 49.67 ± 1.52 |
| 4 mg/kg | 22.60 ± 1.40 | 50.01 ± 2.59 |

TABLE II-continued

Anesthetic and Respiratory Effect of
Nalbuphine, Morphine and
Nalbuphine plus Morphine

| | MAC Reduction % (Mean ± SEM) | $PaCO_2$ - mmHg (Mean ± SEM) |
|---|---|---|
| 8 mg/kg | 28.75 ± 0.98 | 52.80 ± 1.91 |

*From a previous study.

As can be seen from Table II, the 22% reduction in anesthetic requirement by morphine alone in a dose of 2 mg/kg is comparable to that previously reported (Hoffman and DiFazio, *Arch. Int. Pharmacodyn. Ther.*, 1970; 186: 261–268). Morphine at this dose produced a mean $PaCO_2$ in the animals studied significantly higher than that seen with the comparable MAC reduction dose of nalbuphine. The administration of morphine in a dose of 2 and 4 mg/kg during continuous nalbuphine infusion giving peak nalbuphine anesthetic effect resulted in no further reduction in anesthetic requirement. A morphine dose of 8 mg/kg gave a further 5% reduction in anesthetic requirement. The $PaCO_2$ did not increase significantly after the addition of morphine to nalbuphine except at 8 mg/kg.

EXAMPLE 3

Nalbuphine hydrochloride was used as a supplement to oxymorphone or hydromorphone used in the anesthesia of human patients undergoing various types of surgery. The nalbuphine was administered parenterally as each patient was coming out of the anesthesia. The emergence was smooth, rapid and analgesia was maintained for 8-12 hours. The respiratory effect of the nalbuphine was established by measurement of arterial $PaCO_2$ using a blood gas analyzer well known in respiratory therapy. Normal $PaCO_2$ is in the range of 35-42 mmHg. All arterial samples were obtained on an inspired oxygen concentration of 100%. No patient was hypoxic, nor was there any significant shunt present. Respiratory acidosis present before the administration of nalbuphine was completely reversed, pH values being 7.35±0.6 after 0.1 mg/kg of nalbuphine.

The results are shown in Table III.

As can be seen from Table III, respiratory depression resulting from the narcotic was reversed in all cases after the administration of nalbuphine.

What is claimed is:

1. A method of producing analgesia in a mammal comprising administering to a mammal an analgesic dose containing about 1–100 mg of nalbuphine or a pharmaceutically suitable salt thereof and an analgesic dose containing a narcotic analgesic selected from:
   (a) about 1–100 mg of morphine or a pharmaceutically suitable salt thereof;
   (b) about 0.1–20 mg of oxymorphone or a pharmaceutically suitable salt thereof;
   (c) about 0.5–50 mg of oxycodone or a pharmaceutically suitable salt thereof; or
   (d) about 0.1–20 mg of hydromorphone or a pharmaceutically suitable salt thereof.

2. The method of claim 1 wherein the narcotic analgesic and the nalbuphine are parenterally sequentially administered.

3. The method of claim 1 wherein the narcotic analgesic and the nalbuphine are parenterally simultaneously administered.

4. The method of claim 1 wherein the narcotic analgesic and the nalbuphine are orally simultaneously administered.

5. An analgesic composition which comprises per analgesic dose of the composition about 1–100 mg of nalbuphine or a pharmaceutically suitable salt thereof and:
   (a) about 1–100 mg of morphine or a pharmaceutically suitable salt thereof;
   (b) about 0.1–20 mg of oxymorphone or a pharmaceutically suitable salt thereof;
   (c) about 0.5–50 mg of oxycodone or a pharmaceutically suitable salt thereof; or
   (d) about 0.1–20 mg of hydromorphone or a pharmaceutically suitable salt thereof.

6. A composition of claim 5 in oral dosage form.

7. A composition of claim 5 wherein each analgesic dose is in oral dosage form and contains about 5–60 mg of nalbuphine or a pharmaceutically suitable salt thereof and about 5–60 mg of morphine or a pharmaceutically suitable salt thereof.

TABLE III

| TYPE OF SURGERY | AGE | WEIGHT (KG) | NARCOTIC USED | TOTAL DOSE | $PaCO_2$ BEFORE NALBU-PHINE | $PaCO_2$ AFTER 0.1 mg/kg |
|---|---|---|---|---|---|---|
| Thoracotomy | 55 | 85 | Oxymorphone | 15 mg. | 64 | 46 |
| L. Femoral-Popliteal graft | 62 | 74 | Hydromorphone | 12 mg. | 69 | 47 |
| Exploratory Laporatomy | 45 | 48 | Oxymorphone | 6 mg. | 63 | 42 |
| Turb | 72 | 68 | Oxymorphone | 7.5 mg. | 66 | 45 |
| Abdominal Hysterectomy | 48 | 78 | Hydromorphone | 10.5 mg. | 70 | 41 |
| Cholestectomy | 52 | 89 | Hydromorphone | 14 mg. | 61 | 43 |
| Aortic Tube graft | 57 | 83 | Oxymorphone | 8.0 mg. | 67 | 44 |
| Laryngectomy | 67 | 96 | Hydromorphone | 16 mg. | 68 | 43 |
| Bilroth I | 34 | 59 | Oxymorphone | 7.5 mg. | 59 | 46 |
| Thoracotomy | 59 | 77 | Oxymorphone | 13.5 mg. | 62 | 40 |
| Bowel Resection | 66 | 71 | Hydromorphone | 9.0 mg. | 57 | 45 |
| Abdominal Hysterectomy | 48 | 70 | Oxymorphone | 7.5 mg. | 67 | 46 |
| Cholestectomy | 52 | 75 | Hydromorphone | 8.0 mg. | 66 | 43 |
| Exploratory Laporatomy | 44 | 63 | Oxymorphone | 9.0 mg. | 58 | 47 |
| Lumber Fusion | 38 | 73 | Oxymorphone | 12 mg. | 69 | 44 |

8. A composition of claim 5 wherein each analgesic dose is in oral dosage form and contains about 5-60 mg of nalbuphine or a pharmaceutically suitable salt thereof and about 0.5-10 mg of oxymorphone or a pharmaceutically suitable salt thereof.

9. A composition of claim 5 wherein each analgesic dose is in oral dosage form and contains about 5-60 mg of nalbuphine or a pharmaceutically suitable salt thereof and about 2.5-30 mg of oxycodone or a pharmaceutically suitable salt thereof.

10. A composition of claim 5 wherein each analgesic dose is in oral dosage form and contains about 5-60 mg of nalbuphine or a pharmaceutically suitable salt thereof and about 0.5-10 mg of hydromorphone or a pharmaceutically suitable salt thereof.

* * * * *